United States Patent [19]

Ritchey et al.

[11] 4,416,867
[45] Nov. 22, 1983

[54] ORAL COMPOSITIONS

[75] Inventors: Thomas W. Ritchey, Norwood; John M. Weaver, Glen Rock; Martin Sapone, Tenafly, all of N.J.

[73] Assignee: Lever Brothers Company, New York, N.Y.

[21] Appl. No.: 347,597

[22] Filed: Feb. 10, 1982

Related U.S. Application Data

[60] Division of Ser. No. 235,247, Feb. 17, 1981, Pat. No. 4,339,432, which is a continuation-in-part of Ser. No. 50,392, Jun. 20, 1979, abandoned, which is a continuation-in-part of Ser. No. 50,393, Jun. 20, 1979, abandoned.

[51] Int. Cl.$^3$ ............................................. A61K 7/16
[52] U.S. Cl. ................................................. 424/49
[58] Field of Search .................................. 424/49–58

[56] References Cited

U.S. PATENT DOCUMENTS

| | | | |
|---|---|---|---|
| 1,767,667 | 6/1930 | Gray | 424/145 X |
| 2,527,686 | 10/1950 | Sandberg | 167/93 |
| 3,095,396 | 6/1963 | Mantz | 260/29.4 |
| 3,622,662 | 11/1971 | Roberts et al. | 424/54 |
| 3,655,868 | 4/1972 | Vagebas | 424/54 |
| 3,772,431 | 11/1973 | Mlkvy et al. | 424/44 |
| 3,888,976 | 6/1975 | Mlkvy et al. | 424/44 |
| 4,020,158 | 4/1977 | Ashmead et al. | 424/289 X |
| 4,022,880 | 5/1977 | Vinson | 424/49 |
| 4,082,841 | 4/1978 | Pader | 424/50 |
| 4,100,269 | 7/1978 | Pader | 424/49 |
| 4,138,477 | 2/1979 | Gaffer | 424/52 |
| 4,144,323 | 3/1979 | Lamberti | 424/54 |
| 4,146,607 | 3/1979 | Ritchey | 424/54 |
| 4,152,418 | 5/1979 | Pader | 424/50 |
| 4,160,821 | 7/1979 | Sipos | 424/49 |
| 4,339,432 | 7/1982 | Ritchey et al. | 424/49 |

OTHER PUBLICATIONS

C.A. 68 #67077c #67078d, (1968) 70 #94675u (1969) 73 #75863z, (1970), 74 #115918a, #117346g (1971) 80 #74331g, #137182g, (1974) 81 #6271h, #41356m, (1974), 82 #29947t, (1975), 84 #29548e, (1976) 87 #166391z, (1977).

S. Wah Leung "A Method for the In vitro Production of Dental Calculus", J. Periodontology, 28:217, (1956).

Primary Examiner—Shep K. Rose
Attorney, Agent, or Firm—James J. Farrell

[57] ABSTRACT

The astringency of an oral composition containing biologically active zinc ions may be reduced by the addition of glycine to the composition, and adjustment of the pH to 4.5 to 8. In addition, zinc ions may be kept in a biologically active solution at this pH by the addition of glycine. The zinc-glycine combination serves as an anticalculus-antiplaque agent in oral compositions.

9 Claims, No Drawings

ORAL COMPOSITIONS

This application is a divisional application of Ser. No. 235,247 filed Feb. 17, 1981 now U.S. Pat. No. 4,339,432 which is a continuation-in-part application of Ser. No. 050,392 filed June 20, 1979 which is a continuation in part of Ser. No. 050,393 filed June 20, 1979 both applications now abandoned.

BACKGROUND OF THE INVENTION

This invention relates to the field of oral products, particularly to toothpaste and mouthwash compositions.

It has been known to incorporate zinc salts into oral products for a variety of reasons. U.S. Pat. No. 2,527,686 discloses a mouthwash with zinc chloride, with no reason disclosed for its addition. U.S. Pat. No. 3,622,662 discloses zinc oxide and zinc phosphate as stabilizers in a dental cream. U.S. Pat. Nos. 3,772,431 and 3,888,976 disclose mouthwash tablets containing zinc salts as astringent-desensitizing agents. U.S. Pat. No. 3,095,396 discloses dentifrices with zinc salts added to inhibit the dissolving action of sodium metaphosphate.

The zinc ion has also been discovered to have anticalculus and antiplaque properties. The action of the zinc ion is discussed in U.S. Pat. No. 4,082,841, which relates to zinc salts in combination with enzymes. U.S. Pat. No. 4,022,880 discloses combinations of zinc salts with antibacterial agents, and U.S. Pat. No. 4,146,607 discloses zinc salts in combination with tetradecylamine. The antiplaque and anticalculus properties of zinc carboxymethyloxysuccinate are discussed in U.S. Pat. No. 4,144,323.

Despite the foregoing disclosures, the incorporation of zinc into oral products has posed some problems. The most soluble and highly ionized salts of zinc have the greatest bioactivity, zinc chloride being an example. However, due to the extremely small solubility product of zinc hydroxide ($1.2 \times 10^{-17}$), ionized zinc salts can only be kept in solution under acid conditions. Zinc chloride, for instance, must be kept at a pH less than 4.5. This presents some difficulty in formulation of a product with zinc salts, as it may be difficult to use desired ingredients that would raise the pH. Low pH also presents some problems with respect to the sour taste.

Certain zinc salts, such as the phenolsulfonate disclosed in U.S. Pat. No. 4,022,880, and the carboxymethyloxysuccinate disclosed in U.S. Pat. No. 4,144,323 are less sensitive to pH change, and may be formulated in compositions having a pH range of 5 to 6.5. It has been discovered, however, that due to a slight interaction between the phenolsulfonate and cationic germicides, for instance, cetyl pyridinium chloride, the latter being a germicide also disclosed in U.S. Pat. No. 4,022,880, there is reduced germicidal activity.

Another problem of formulating an oral product with zinc salts is astringency, an organoleptically displeasing effect on the zinc ion. While certain of the aforementioned U.S. patents use zinc for its astringent properties, the astringency is not always desirable, and can be objectionable when the zinc salt is used at higher levels for more effective calculus control. U.S. Pat. No. 4,082,841 recommends using insoluble zinc salts to reduce astringency, while U.S. Pat. No. 4,144,323 discloses zinc carboxymethyloxysuccinate as a less astringent, but soluble zinc compound.

It has been discovered that the foregoing problems have been overcome by the instant invention, which is an oral composition containing zinc kept in solution at pH 4.5-8 using glycine. Applicants have discovered that when glycine is added to a solution containing biologically active zinc, the pH may be raised as high as 8.0 without precipitation of zinc hydroxide. There is also no interaction with germicides. The astringency of the mouthwashes may be substantially reduced to near neutral pH's and also by raising the pH of the zinc-glycine combination, the astringency of the zinc is greatly reduced. Further, when glycine is added to a solution of biologically active zinc, the pH may be raised as high as 8.0 without precipitation of zinc hydroxide.

The use of glycine in an oral product is described in U.S. Pat. No. 3,655,868. The patent discloses the addition of glycine to copper gluconate in order to prevent the absorbtion of the gluconate by mucin in the mouth. The combination is also soluble at near neutral pH's, whereas the previously used copper gluconate-amino benzoate combination is not. The patent discloses that its usefulness lies in the presence of complexes of both gluconate and glycine. The instant invention requires no particular anion.

Applicants have discovered that zinc ions may be kept in a biologically active solution at a pH of about 4.5 to about 8.0 by the addition of glycine and that the astringency of an oral composition containing biologically active zinc may be reduced by the addition of glycine to the composition and by adjusting the pH to a range of from 4.5 to about 8.0. In this pH range, the solution, biologically active zinc, is far less astringent than at a pH of below about 4.5. At a pH above, about 8.0, the solubility of the zinc is greatly reduced and precipitation of zinc hydroxide is likely. Accordingly, an oral composition is provided having a pH of about 4.5 to about 8.0, comprising a physiologically acceptable zinc salt and glycine.

Glycine, also known as aminoacetic acid, is an amino acid of the formula:

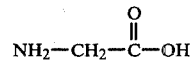

Glycine has been used as a nutrient and is non-toxic. It is also an excellent buffer and a natural sweetening agent. The concentration of glycine in the invention will vary from about 0.01% to about 4%, preferably from 0.1% to 1.0% by weight, depending on zinc ion concentration and desired pH, although there are no reasons why glycine cannot be used at higher levels, since it is a non-toxic sweetening agent.

The zinc salts, according to the present invention, will generally be present in the oral composition in an amount of from about 0.04% to about 2.0%. In the case of mouthwash products, the zinc salt may be added at a level of about 0.04% to about 0.7% by weight of soluble zinc ion, with 0.04% being the approximate minimum active concentration and 0.7% being the approximate concentration at which astringency becomes objectionable. The preferred concentration of zinc ion in a mouthwash is 0.1%–0.3%, and 0.2% to 3% in a toothpaste. By adding glycine and raising the pH, however, the level of zinc may be raised without objectionable astringency.

Any pharmaceutically acceptable zinc salt may be used, among them acetate, benzoate, borate, bromide, carbonate, citrate, chloride, glycerophosphate, hexafluorosilicate, dl-lactate (trihydrate), nitrate, phenolsulfonate, silicate, alkanoates having 8–18 carbon atoms, salicylate, stannate, sulfate, tannate, tartrate, titanate, tetrafluoroborate, oxide, peroxide and hydroxide. The zinc compounds may be used singly or in admixture.

The zinc salts may be added to the mouthwash or product as zinc glycinate directly, although the zinc salt and the glycine are usually added separately for convenience. The term "pharmaceutically acceptable" as used herein with reference to zinc compounds is applicable to those compounds which, under the conditions of use and in the compositions set forth herein, are safe and organoleptically tolerable in the oral cavity, and have no significant side effects either orally or systemically.

The balance of the oral composition in accordance with the present invention will consist of the usual carrier media and other desired substances consistent with the form it is in. For example, where the oral composition contemplated is a mouthwash, the balance of the preparation will usually contain water, or water and a mono- or polyhydric alcohol such as ethanol, glycerol, or sorbitol, and optionally, flavoring substances and foaming agents. Glycerol and sorbitol are also useful as an aid in sweetening the product. Surfactants and/or suspending agents are usually present in mouthwashes as solubilizers for essential flavoring oils. The customary solubilizers for this purpose are the sorbitan fatty acid esters, the polyoxyethylene derivatives thereof, and polyoxyethylene fatty acid ethers. In addition, the mouthwash formulation may contain one or more of the well known, highly active antibacterial agents, such as bisbiguanides, aliphatic amines, hexachlorophene, the salicylanilides, compatible quaternary ammonium compounds, and the like.

When the oral composition is in the form of a toothpaste, there may be present polishing agents, humectants, bodying agents, flavoring substances, sweetening substances, foaming agents, etc. It will be understood that the polishing agents and other components suitable for use in the toothpastes of the invention must be compatible with the zinc compounds.

Among the suitable inorganic polishing agents useful in accordance with the invention are the silica xerogels and silica aerogels manufactured by the Davidson Chemical Division of W. R. Grace and Company, for example those available under the trade names of Syloid 63 and Syloid 65 (xerogels), and Syloid 244 (aerogels). The xerogels are synthetic, aggregated, amorphous, highly porous silicas having generally a mean particle diameter of about 4 to about 10 microns. The aerogel Syloid 244 has a mean particle diameter of about 3 microns and is more porous than the xerogels. Also useful are other polishing agents disclosed hereinafter.

The polishing agent should be in the form of fine particles, as is well known in the art. Preferably, the particles should be of such size that at least 40% pass through a 325 mesh screen, and at least 90% pass through a 20 mesh screen. The finer particles within this size range are preferred, particularly a size distribution such that all the particles pass through a 20 mesh screen; more than 90% pass through a 100 mesh screen; more than 80% pass through a 200 mesh screen, and more than 40% pass through a 325 mesh screen. Especially preferred are the finer particles having a mean particle diameter of about 3 to about 44 microns.

Polymer particles of various types are useful as abrasives. A particularly useful polymer is polyethylene in powder form of such size that more than 40% passes through a 325 mesh screen; more than 80% passes through a 200 mesh screen; at least 85% passes through a 100 mesh screen; and 90 to 100% passes through a 20 mesh screen. Such polyethylene polymers are sold under the trade names Super Dylan Polyethylene J-1 or J-2 powder, available from ARCO/Polymers, Inc.

Other substances proposed as dental abrasives include various abrasive materials such as silica embedded in protective plastic particles, chalks, metaphosphates, abrasives, and dicalcium phosphate dihydrate.

Polishing agents will be present in the toothpastes of the invention over the broad range of about 1% to 70%, preferably 10% to 60%, and typically from about 20% to 50%. In a tooth powder the polishing agent will be present over the range of about 50% to 99%, preferably from about 70% to 95%, and typically from about 90% to about 95%.

The toothpastes will usually contain compatible bodying agents such as gum Karaya, gum Tragacanth, starch, sodium carboxymethylcellulose, Irish moss, gum arabic, sodium carboxymethylhydroxyethylcellulose, polyvinylpyrrolidone, etc. When present, these will usually be at levels of from about 0.5% to about 3%, preferably from about 0.8% to about 1.5%.

Humectants are desirable in a toothpaste to provide smooth texture and flowability. These will usually be such compounds as glucose, honey, glycerol, propylene glycol, sorbitol, polyethylene glycol 400, and other polyhydric alcohols, and may be present in the composition in amounts of up to about 80% by weight.

Other adjuvants may be present, such as fluorides, chlorophyll compounds, flavoring substances, saccharin, urea, ammonium compounds, alcohol, mineral oil, and foaming agents or detergents, such as sodium lauryl sulfate, dodecanesulfonate, acyl taurines, acyl isethionates, etc., depending upon the form of the product.

The various chemical compounds present in the oral compositions may themselves result in attainment of the desired pH of about 4.5 to about 8.0. If the pH of the formulation remains below 4.5, any alkaline material suitable for use in an oral composition and compatible with the other ingredients may be used to adjust the pH. Sodium hydroxide, sodium carbonate and sodium bicarbonate are typical. If the pH is above about 8.0, where precipitation of zinc hydroxide is likely, any acid buffer, suitable for use in an oral composition and compatible with the other ingredients, may be added. Examples are hydrochloric acid and citric acids.

Oral products containing the zinc-glycine mixture may, in addition, contain other ingredients identified as acting synergistically with the zinc to prevent calculus and plaque, such as the antibacterial agents of U.S. Pat. No. 4,022,880 and the enzymes of U.S. Pat. No. 4,082,841.

The invention is illustrated by the following Examples. All percentages herein are by weight.

EXAMPLE 1

Solubility Testing

To aqueous solutions of zinc chloride at levels of 0.172% (0.0126 M) and 0.344% (0.0252 M), were added glycine at levels of 0.1% (0.0132 M), 0.2% (0.0266 M), 0.4% (0.0432 M), and 0.8% (0.106 M). The pH of each solution was raised from 4 to 8 with NaOH, and the point at which $Zn(OH)_2$ precipitated was noted. The results are given in Table 1 below.

TABLE 1

| ZnCl$_2$ | 0 | (.0132M) .1% | (.0266M) .2% | (.0532M) .4% | (.106M) .8% | glycine |
|---|---|---|---|---|---|---|
| 0.172% (.0126M) | p = 4.8 | p = 7-8 | p = 7-8 | * | * | |
| 0.344% | p = 4.8 | p = 6.5 | p = 6.5 | p = 6.5 | p = 6.5 | | p = pH of precipitation.
* = stable at pH 8.

EXAMPLE 2

Solutions were prepared with 0.172% ZnCl$_2$ and glycine at levels of 0.1%, 0.2%, 0.4% and 0.8% at pH's of 4.8, 5.5 and 6.5. All solutions remained stable over a 6 week period with no precipitation.

EXAMPLE 3

An in vitro dipping test was used to determine whether the zinc ion with glycine was an effective anticalculus agent. The basic test is described in an article by S. Wah Leung, "A New Method For The In Vitro Production of Dental Calculus," *J. Periodontology*, 28:217 (1956), and is modified as described herein.

The creation of dental calculus was simulated on frosted glass plummets by continuously dipping them in a calcifying solution. Each dipping cycle consisted of a 30 second immersion in the solution followed by 30 seconds air drying. The dipping apparatus was enclosed in a constant temperature cabinet at 36°±1° C. at high humidity.

Daily anticalculus treatment consisted of 5 minutes dipping in distilled water, 1 minute immersion in a test solution and another 5 minute dipping in distilled water. Dipping in a calcifying solution as described above is then repeated.

The calcifying solution is made with porcine glycoprotein, which has similar properties to human mucin. The submaxillary gland of a pig is minced, extracted three times with water in a Waring Blender for five minutes each, stirred at low speed for 18 hours, centrifuged in 250 ml bottles at at least 15,000 G for 30 minutes, and lyophylized in a Stoken Freezer Dryer for two days. All procedures were carried out at 4° C. The mucin is dessicated in 5 gm quantities at 40° C.

A new calcifying solution is prepared each day by adding the lyophylized mucin at 135 ml CaCO$_3$ solution and 15 ml PO$_4$ buffer, then bubbling with CO$_2$ until the mucin is dissolved. The CaCO$_3$ solution is prepared by adding 0.070 grams of CaCO$_3$ to 540 ml water, and bubbling with CO$_2$ until the carbonate dissolves. The phosphate buffer (pH=7) is a mixture of 8 grams NaH$_2$PO and 9.47 grams Na$_2$HPO$_4$ in one liter of water.

After 8 days of dipping, the plummets are dessicated for 24 hours at 40° C., and analyzed for calcium and phosphorous. The Ca/P ratio is determined and compared with the ratios for actual dental calculus, which vary from 1.28 to 1.55.

The results of the dipping test are shown in Table 2 below. For comparison, results for zinc carboxymethyloxysuccinate [Zn$_3$(CMOS)$_2$], which may be formulated at a higher pH than zinc chloride, are also given.

TABLE 2

| | conc. | pH | Ca/P |
|---|---|---|---|
| H$_2$O | 100% | 5.3 | 1.25 |
| CPC | .04% | 5.3 | 1.30 |
| ZnPS.8 H$_2$O | .67% | 5.3 | 0.83 |
| ZnCl$_2$ | .172% | 4.3 | 0.81 |
| ZnCl$_2$ + glycine | .172% .5% | 5.3 | 0.85 |
| ZnCl$_2$ + glycine + CPC | .172% .5% .04% | 5.3 | 0.85 |
| Zn$_3$(CMOS)$_2$ | .2% | 5.3 | 1.13 |

ZnPS = zinc phenolsulfonate
CPC = cetyl pyridinium chloride

EXAMPLE 4

Astringency Testing

Four mouthrinses were prepared with the following compositions:

| Rinse A | Zinc chloride | 0.172% |
|---|---|---|
| | HCl | to pH 4.3 |
| | Water | Balance to 100% |
| Rinse B | Zinc chloride | 0.172% |
| | Glycine | 0.500% |
| | NaOH | to pH 4.3 |
| | Water | Balance to 100% |
| Rinse C | Zinc chloride | 0.172% |
| | Glycine | 0.500% |
| | NaOH | to pH 7.2 |
| | Water | Balance to 100% |
| Rinse D | Zinc chloride | 0.172% |
| | Glycine | 0.500% |
| | Na$_2$CO$_3$ | to pH 7.2 |
| | Water | Balance to 100% |

Ten subjects compared these rinses on three consecutive days. A and B were compared on day 1, B and C on day 2, and C and D on day 3. All subjects rinsed with ml of each rinse for 30 seconds. The two rinses were sampled by each subject four hours apart.

No significant differences were found in astringency between Rinses A and B, or C and D. However, Rinses B and C showed a significant difference from each other, Rinse C being much less astringent.

Both Rinses B and C contained zinc and glycine, the difference between the two being the pH. The presence of glycine enabled the pH to be raised to a point where the zinc was less astringent. No improvement was noted by the substitution of sodium carbonate for sodium hydroxide as the buffer.

Examples 5 and 6 set forth a mouthwash according to the invention herein.

EXAMPLE 5

| Mouthwash | |
|---|---|
| Ingredient | % weight |
| Ethanol | 22.00% |
| Glycerol | 12.00 |
| Flavor, color | .90 |
| Zinc Chloride | .25 |
| Glycine | .80 |
| Cetyl pyridinium chloride | .05 |
| Polyoxyethylene (20) Sorbitan monolaurate* | .20 |
| NaOH | to pH 6.5 |
| Water | Balance to 100% |

*Marketed by Hodag Chemical Company as Polysorbate 20, and Atlas Chemical Co. as Tween 20.

EXAMPLE 6

| Mouthwash | |
|---|---|
| Ingredient | % weight |
| Glycerol | 8.00% |
| Flavor | .15 |
| Saccharin | .02 |
| FD&C Yellow No. 6 (.7% solution) | .10 |
| FD&C Red No. 2 (.2% solution) | .12 |
| Zinc sulfate | .40 |
| Glycine | 1.80 |
| Sodium lauryl sulfate | .33 |
| Polyoxyethylene (20) Sorbitan monolaurate | .30 |
| NaOH | to pH 7.2 |
| Water | Balance to 100% |

Examples 7 and 8 set forth a toothpaste according to the invention herein.

EXAMPLE 7

| Toothpaste | |
|---|---|
| Ingredient | % weight |
| Silica Xerogel Syloid 63) | 10.00 |
| Humectant (Sorbitol) | 40.00 |
| Sodium Lauryl Sulfate (21% in glycerine) | 7.00 |
| Bodying Agent (Na Carboxymethylcellulose) | 1.00 |
| Flavor, color | 1.50 |
| Zinc chloride | 1.00 |
| Glycine | 2.00 |
| NaHCO$_3$ | to pH 6.0 |
| Water | Balance to 100% |

EXAMPLE 8

| Toothpaste | |
|---|---|
| Ingredient | % weight |
| Silica Xerogel (Syloid 63) | 15.00 |
| Powdered Polyethylene* | 5.00 |
| Na Carboxymethylcellulose | .80 |
| Glycerol | 65.00 |
| Saccharin | .20 |
| Zinc chloride | .60 |
| Glycine | 1.50 |
| Flavor | 1.30 |
| Coloring agent | .25 |
| Foaming agent | .65 |
| NaOH | to pH 6.3 |
| Water | Balance to 100% |

*High density polyethylene powder, average particle size 8-9 microns.

The invention has been described with respect to certain preferred embodiments. Various modifications and variations in lieu thereof will be suggested to persons skilled in the art, and are to be included within the spirit and purview of this application and within the scope of the appended claims.

What is claimed is:

1. A toothpaste composition having a pH of about 4.5 to about 8.0 comprising a physiologically acceptable zinc salt or zinc glycinate in an amount sufficient to provide about 0.2% to about 3% by weight of the composition of soluble zinc ions wherein said zinc salts may have a tendency to produce the organoleptically displeasing effect of astringency; and glycine at a level of about 0.1% to about 4% by weight, based on the total weight of the composition as the essential effective agent reducing astringency or said glycine serving to effectively solubilize said zinc salts at a pH of about 8 or above.

2. The composition according to claim 1 wherein the zinc salt is zinc chloride.

3. The composition according to claim 1 wherein the zinc salt is present in an amount sufficient to provide a level of soluble zinc ions of about 0.1% to about 0.3% by weight.

4. The composition according to claim 1 wherein the glycine is present at a level of about 0.1% to about 1% by weight.

5. The composition according to claim 1 wherein the zinc salt is at a level of about 0.04% to about 2.0% by weight.

6. A method for reducing the astringency of a toothpaste composition containing biologically active zinc ions in an amount of about 0.2% to about 3% by weight of the composition comprising adding glycine to said composition in an amount of from about 0.01% to about 4% by weight and adjusting the pH of said composition to about 4.5 to about 8.0, or above.

7. The method defined in claim 6 wherein the zinc ions are supplied by zinc chloride.

8. The method defined in claim 6 wherein the pH is adjusted to about 7.

9. The method of claim 6 wherein the pH is adjusted with sodium carbonate.

* * * * *